United States Patent [19]

Springer

[11] 4,045,554
[45] Aug. 30, 1977

[54] PROCESS FOR PRESERVING WOOD CHIPS DURING STORAGE

[75] Inventor: Edward L. Springer, Madison, Wis.

[73] Assignee: The United States of America as represented by the Secretary of Agriculture, Washington, D.C.

[21] Appl. No.: 618,187

[22] Filed: Sept. 30, 1975

[51] Int. Cl.² ............... A01N 13/00; A61L 13/00
[52] U.S. Cl. ................... 424/164; 424/230; 424/346; 424/348; 426/532
[58] Field of Search ............. 424/162, 164, 346, 348

[56] References Cited

U.S. PATENT DOCUMENTS

| | | | |
|---|---|---|---|
| 1,006,077 | 10/1911 | Friedemann | 424/346 X |
| 2,196,988 | 4/1940 | Heath et al. | 424/348 |
| 2,599,373 | 6/1952 | Chrzanowski | 424/348 X |

OTHER PUBLICATIONS

Gregory–Uses & Applications of Chemicals & Related Materials, p. 528 (1939).

*Primary Examiner*—Leonard Schenkman
*Attorney, Agent, or Firm*—M. Howard Silverstein; David G. McConnell

[57] ABSTRACT

A process which limits the loss of wood substances, brightness and tall oil in wood chips during storage. The process involves treating wood chips with a dilute aqueous solution of sodium bisulfite and a phenol. This treatment effectively prevents chip pile heating and microbial growth and thus limits chip deterioration and brightness loss while preserving tall oil. The process is also effective with any other moist plant-derived raw material.

2 Claims, No Drawings

4,045,554

PROCESS FOR PRESERVING WOOD CHIPS DURING STORAGE

BACKGROUND OF THE INVENTION

1. Field of the Invention

This invention relates to the preservation of moist plant-derived raw materials. More particularly the invention relates to the preservation of wood substance, brightness and inherent tall oil in wood chips during stockpiling.

2. Description of the Prior Art

Outside storage of wood chips, introduced in the early 1950's, resulted from the need to stockpile chips produced from residues of sawmills and veneer plants. As the economic advantages of handling wood as a bulk material become apparent, many mills began chipping and stockpiling chips as an alternative to log storage.

With increased use of this method for handling and storage of wood, a serious disadvantage became apparent. Stockpiled wood chips characteristically lose wood substance, brightness, and tall oil during storage.

One principal difference between log and chip storage is that a significant amount of heat is evolved in piled chips but not in piled logs. Center temperatures in chip piles frequently reach and remain in the vicinity of 150° F. thus resulting in deterioration of the material.

Heat production in chip piles is primarily caused by the respiration of a rapidly multiplying population of bacteria, the enzymatic respiration of any living wood cells, respiration of fungi and direct chemical oxidation. Prevention of the heat release from bacteria, fungi and living wood cells would stop the initial temperature rise and prevent the direct chemical reactions from releasing any significant amount of heat.

A chemical treatment used to prevent chip deterioration and resulting loss in tall oil should reduce the initial heating by inhibiting respiration of bacteria and fungi and additionally the respiration of any living wood cells that are present. A treatment that kills the bacteria, fungi and the living wood cells would be highly effective. The chemical treatment should also meet the following criteria. It should be effective for a reasonable length of time and its cost should be less than the losses incurred from chip deterioration. It should be compatible with the pulping process, should not cause pollution, and obviously should not be hazardous to personnel who handle and apply it. When used with foodstuffs such as wheat or corn, the treatment must meet the additional requirement of being nontoxic to humans and animals.

One method that has been found successful in reducing wood substance losses in stored wood chips, by limiting the effect of wood-destroying fungi on the chips, can be found in U.S. Pat. No. 3,646,196. This method inherently produces a large reduction in wood brightness and has little favorable effect on tall oil retention. A subsequent development, disclosed in application Ser. No. 431,762 filed Jan. 8, 1974, now abandoned, uses sodium N-methyldithiocarbamate. In addition to reducing wood substance losses this treatment retards brightness losses. The present invention, however, works effectively against all three major effects of deterioration, i.e., wood substance, brightness and tall oil losses. With the cost of tall oil as high as it is today, the preservation of this product during wood chip storage is vital.

Sodium bisulfite has been used as a preservative with wood and is effective for a limited period (about one month according to the inventor's tests). Phenolic compounds have also been used to preserve various cellulosic materials but are ineffective in reducing heat buildup in chip piles. The present invention has combined these two chemicals into a treatment which far surpasses in effectiveness either of these components individually or what one skilled in the art would have expected their combined effectiveness to be.

SUMMARY OF THE INVENTION

This invention provides a preservative treatment for moist plant-derived materials. Exemplifying the material with which the treatment is effective is wood chips. The treatment is also effective when used with wheat, corn, straw, sugar cane bagasse, and other carbohydrate-based materials. Initial deterioration occurs because of chip pile heating caused by wood cell respiration and the growth of micro-organisms. A chemical treatment comprising a dilute aqueous solution of sodium bisulfite and a phenol was found to kill or drastically inhibit the growth of bacteria and fungi on treated chips and to inhibit wood cell respiration. Treatment of the chips, or other material to be treated, can be accomplished by spraying, immersing, or any other means available for getting the solution onto the material. Treatment level is determined by the uptake of the treating solution and the percentage of the components in the solution.

A wide range of phenols have been tested and found effective when used in this treatment, e.g., o-cresol, p-cresol, sodium o-phenylphenol, hydroquinone, resorcinol, P-nitrophenol and 2,4-dinitrophenol. Salicylic acid has also been used which has the additional advantage of being nontoxic to humans and animals.

Accordingly, the primary objects of this invention are to provide a treatment to reduce losses in wood substance, brightness and tall oil in wood chips during storage. Another object is a preservative treatment for all moist plant-derived materials. A further object is the provision of a chemical treatment for inhibiting the growth of bacteria, fungi and respiration of wood cells in the stockpile of wood chips which is economical, longlasting and more effective than mechanical or other chemical methods.

DESCRIPTION OF THE PREFERRED EMBODIMENTS

To further illustrate this invention, the following examples are given:

EXAMPLE I

The influence of potential control chemicals on the release of initial heat of fresh wood chips was studied by placing chips in insulated boxes and observing the temperature profiles at the center of the samples. The boxes, constructed of polystyrene foam, had an internal volume of 3.9 cubic feet or 0.11 cubic meters (inside dimensions 22½ by 13½ by 22 inches or 57 by 34 by 56 centimeters) with a wall thickness of 2½ inches or 6.4 centimeters. Each box was fitted with air inlet and outlet manifolds and was fed water-saturated air at ambient temperature at a measured rate. Copper-constantan thermocouples, placed in the center of the chip mass, were used to measure temperatures. Because temperature profiles of untreated chips cannot be satisfactorily duplicated, presumably because of changes in the wood with time, untreated control samples were run with every treated sample.

Fresh aspen chips were immersed for about 10 minutes in an aqueous solution of 2.0% sodium bisulfite and 0.70% o-cresol and were then drained. The chips were stored in the insulated boxes described above. The treated chips showed no heating or microbial growth after three months storage, while the control box showed a substantial number of micro-organisms and a resulting temperature increase.

This procedure was repeated with the same results using 2.0% sodium bisulfite with the following phenols:
0.70% p-cresol
0.60% sodium o=phenylphenol
0.35% hydroquinone
0.35% resorcinol
0.30% p-nitrophenol
0.30% 2,4-dinitrophenol
0.52% salicylic acid When 0.6% phenol was used with 2.0% sodium bisulfite there was no heating during the three month period and only a slight trace of micro-organisms.

EXAMPLE II

Further evaluation of the 2.0% sodium bisulfite and 2,4-dinitrophenol mixture was carried out in a chip pile simulator.

Fresh short leaf pine (*Pinus echinata Mill.*) chips were dipped for about 15 seconds in an aqueous solution containing 2.0% sodium bisulfite and 0.3% 2,4-dinitrophenol (a dosage level of 8.1 lb. of NaHSO₃ and 1.2 lb. of 2,4-dinitrophenol per ton of ovendried wood). The chips were then placed in a chip pile simulator. The simulators are 16-foot-high cylinders with 4-foot diameters. Each has a 6-mil polyethylene liner (see Springer et al., Evaluation of Chemicals for Preserving Wood Chips Using Pile Simulators, p. 125, Tappi 56 (6), June 1973). Untreated chips were placed in an identical simulator. One empty simulator volume per day of water-saturated air was continuously passed through each simulator. Temperatures from the centers of the simulators were observed with thermocouples.

Graph 1 shows the temperatures at the geometric centers of the simulators filled with treated and untreated chips during the 180-day storage period. The treatment was highly successful in suppressing heating during the entire storage period. Table I gives the losses in ovendried wood substance at various locations in the simulators at the end of the storage period.

TABLE I

| Sample location | | Sample | Weight loss, % | |
|---|---|---|---|---|
| Vertical, ft from bottom | Cross section, ft from center | size, Kg | Untreated | Sodium bisulfite + 2,4-dinitrophenol |
| 8 | 0 | 0.15 | 9.1 | 0.1 |
|  | 1 | 0.15 | 6.4 | 0.0 |
|  | 2 | 0.15 | 7.2 | 0.2 |
| 10 | 1 | 8 | 9.9 | 0.3 |
| 12 | 0 | 0.15 | 13.6 | 0.4 |
|  | 1 | 0.15 | 12.5 | 0.04 |
|  | 2 | 0.15 | 14.8 | 0.6 |

The treatment was highly effective in preventing weight loss. The initial brightness of the untreated chips was 49%; that of the treated chips 57% (some bleaching occurred). After six months storage, the brightness of the untreated chips was 36% while that of the treated chips was 50%. Thus, although the treated chips lost brightness, they were still as bright after storage as the untreated chips were initially.

Random samples of the initial untreated unstored chips and samples of treated chips from the large sample bags after storage were subjected to kraft pulping under the following conditions:
Active alkali — 16.5%
Sulfidity — 25.0%
Liquor to wood ratio = 4:1
Time to 170° C. = 90 min.
Time at 170° C. = 75 min.

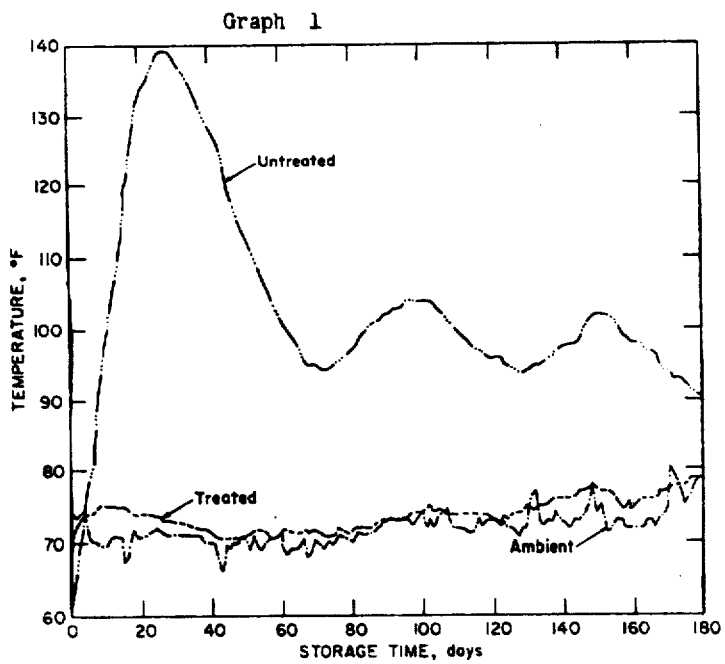

Graph 1

The pulp yield of both kinds of chips was 47% at a Kappa No. of 50. No significant differences in pulp properties were observed.

A representative sample of black liquor from each cook was analyzed for tall oil by the method of Saltsman and Kuiken. The average tall oil content of the initial untreated chips was 47 lb/ton of ovendried wood; that of the untreated stored chips was 9 lb/ton of ovendried wood and that of the treated stored chips 41 lb/ton of ovendried wood. Thus, about 87% of the initial tall oil was retained in the treated chips after 180 days of storage, whereas only 19% remained in the untreated stored chips.

The effect of these solutions at the concentrations examined indicate that the treatment would be effective with as much as 10.0 percent sodium bisulfite and 5.0 percent phenol and if the solutions were sprayed on the material to be treated this could be even higher. The lower limit of effectiveness is calculated to be 0.5 percent sodium bisulfite and 0.05 percent phenol.

These examples demonstrate that this invention prevents or greatly retards initial heat buildup and therefore reduces material deterioration.

Having thus disclosed my invention, I claim:

1. A method for preserving wood substance, brightness and tall oil in stored wood chips comprising treating said chips with a biocidally effective amount of an aqueous solution containing 2.0 percent sodium bisulfite and:
   a. 0.35 percent resorcinol; or
   b. 0.30 percent p-nitrophenol.

2. A method for retarding deterioration in wheat, corn, straw, sugar cane bagasse and wood, comprising treating the material with an aqueous solution containing 2.0 percent sodium bisulfite and:
   a. 0.35 percent resorcinol; or
   b. 0.30 percent p-nitrophenol.

* * * * *